United States Patent [19]
Naggiar

[11] Patent Number: 5,698,187
[45] Date of Patent: Dec. 16, 1997

[54] COLD WAX DEPILATORY COMPOSITION

[75] Inventor: Samir F. Naggiar, Plainsboro, N.J.

[73] Assignee: Carter-Wallace, Inc., N.Y., N.Y.

[21] Appl. No.: 804,502

[22] Filed: Feb. 21, 1997

[51] Int. Cl.⁶ .................................................. A61K 7/155
[52] U.S. Cl. ............................................. 424/73; 424/400
[58] Field of Search ................................... 424/73, 400

[56] References Cited

FOREIGN PATENT DOCUMENTS 2541894  9/1984  France .

*Primary Examiner*—Gollamudi S. Kishore
*Attorney, Agent, or Firm*—Kevin B. Clarke

[57] ABSTRACT

A depilatory composition for the removal of hair from the human body is composed of a mixture of maltodextrin, having a dextrose equivalent of from about 5 to about 36, sucrose, water and citric acid. This mixture is heated to dissolve the solute materials, and then cooled to form a soft, pliant composition which can be manually applied to the skin. When contacted with body hair, the composition firmly adheres to the hair such that when the material is drawn away from the skin, the hair will be removed from its roots without undue swelling or skin irritation.

6 Claims, No Drawings

COLD WAX DEPILATORY COMPOSITION

This invention relates to depilatories, and more particularly relates to a novel and improved depilatory composition of a wax-like consistency which is specifically adaptable for use in removing hair from the human body, such as, for example, eyebrows and other facial hair, legs or arms.

BACKGROUND AND FIELD OF THE INVENTION

The removal of hair from the human body has received considerable attention. The hair and hair follicles can be removed by certain surgical operations or by electrolysis. Also, it is customary to remove hair by the use of tweezers or other instruments but does not have the same long lasting effects as surgical procedures. Moreover, the use of hair removal instruments is generally confined to removal of hair from a localized area, such as, along the eyebrows or nostrils.

Creams or cold waxes have been formulated in the past for the purpose of hair removal to the end of achieving more lasting effects as well as the ability to apply over greater areas than is possible by plucking out individual hairs from a localized part of the body. For example, it has been proposed in the past to employ a combination of honey, rosin and wax which are heated together and thereafter combined with citric acid which is mixed into the composition until it has acquired a creamy texture, reference being made to U.S. Pat. No. 2,091,313 to W. M. Grant. Grant fails to state to what temperature level the formulation is heated. Moreover, the use of a wax composition, such as, beeswax has been found to irritate the skin and to cause redness and swelling.

British Letters Patent No. 901,624 to E. Wenden discloses the formulation of a cream made up of sugar and lemon juice, glycerine, boric acid powder, sodium chloride and a water carrier. These ingredients are heated, then allowed to cool to a temperature at which they may be poured into separate jars or containers, and specifically are heated to a temperature on the order of 278° F. to form a plastic mass. The resultant composition is applied to the skin so as to become matted with the hair, then immediately stripped from the skin to cause removal of the hair with the plastic mass.

Another British Letters Patent No. 1,242,083 to M. Doughty also discloses the combination of sugar with citric acid and water in the formation of a depilatory or hair removal composition. Generally, the approach taken in Doughty is to boil the mixture for a short period or optionally to simmer over longer periods but makes no distinction as to the relative effect of boiling versus simmering. Once again the resultant composition is alleged to be of the consistency of paste and which will not harden when applied to the skin and, being water soluble, can be readily cleaned off of the skin; and Doughty proposes the optional addition either of a gelatin or isinglass. It has been found that the use of gelatin tends to leave a burning sensation when applied to the skin as well as to cause swelling and discoloration. Moreover, the composition of sugar and gelatin as disclosed by Doughty would not appear to possess the capability of removing dead skin cells or of exfoliating the skin so as to leave a natural glow when the process is completed.

U.S. Pat. No. 4,832,949 discloses depilatory compositions made up of a mixture of honey, sugar and citric acid. These compositions must be heated to soften before use.

U.S. Pat. No. 4,842,610 depilatory compositions composed of corn syrup, water and optionally germicides, preservatives and opacifiers.

In the formulation of a depilatory composition, it is highly desirable that the composition can be readily applied with a finger or fingers over a closely controlled area without adhering to the fingers so as to uniformly and firmly adhere to the hair, and can be readily removed by grasping and pulling quickly away from the skin to effect the complete removal of hair over the applied area without necessity of repeating the process. Further, in this connection, it is most desirable that the composition will not cause swelling or other irritation to the skin.

SUMMARY OF THE INVENTION

It is therefore an object of the present invention to provide for a novel and improved depilatory composition for the effective removal of hair from the skin.

Another object of the present invention is to provide for a hair removal composition adaptable for use in removing hair from parts of the human body and can be quickly and easily formulated and produced and possesses good shelf life.

A further object of the present invention is to provide for a novel and improved depilatory composition and method of preparing same which can be applied to closely controlled areas of the human body for the purpose of complete and efficient hair removal from those areas without causing irritation or swelling, is water-soluble and does not cause any substantial discoloration of the skin.

A still further object of the present invention is to provide for a novel and improved depilatory composition which when applied in thin strips is capable of removing dead skin cells along with hair from the human skin, does not require repeated applications to the same area in order to effect complete removal of the hair down to the roots and is long lasting.

In accordance with the present invention, there has been devised a novel and improved depilatory composition which is of a wax-like consistency and can be applied over selected areas of the skin to effect complete hair removal therefrom. In the preferred composition of the present invention, major proportions of sucrose are combined together with minor proportions of maltodextrin and citric acid, the sucrose being present in a greater amount than the maltodextrin, and the ingredients are stirred together over medium heat. The composition is cooked for a time period, depending upon quantities, until the temperature reaches 125° C., but broadly at a temperature level just below that which would cause hardening of the composition. After the cooking operation, the composition is permitted to cool to room temperature and then poured into individual containers. The resultant product will harden somewhat after complete cooling but nevertheless retains its wax-like, pliable consistency.

The product is pressed onto the skin by hand in areas where the hair is to be removed and is worked into the hair so as to assure good adherence to the hair and to the skin over the affected area. Once applied in the manner described, the composition is then quickly stripped or pulled away from the skin with the fingers to effect complete hair removal.

The above and other objects, advantages and features of the present invention will become more readily appreciated and understood from a consideration of the following detailed description of preferred and alternate forms of compositions and procedures for preparing same.

DETAILED DESCRIPTION OF THE PREFERRED EMBODIMENT

In the preparation of the preferred composition of the present invention, a batch of maltodextrin and sucrose were combined with a limited quantity of lemon juice in a large vat. Preferably, from about 5% to about 30% by weight of maltodextrin were combined with about 45% to about 70% by weight of sucrose, preferably from about 14 to about 1 part by weight sucrose per part by weight maltodextrin and optionally from about 0.025% to about 1.0% by weight of citric acid, i.e. lemon juice. The sucrose is a fine granulated sugar. Powdered sugar has not been found to be as effective in the formulation of the compound as granulated sugar.

The maltodextrin employed is a product having a dextrose equivalent (DE) of from about 5 to about 36, preferably from about 16.5 to about 19.5. The preferred composition being a maltodextrin marketed by the Grain Processing Corporation of Muscataine, Iowa, under the Trademark MALTRIN® QD M500.

The dextrose equivalent is the total amount of ordinary sugars expressed as an anhydrous dextrose, present in a dry hydrolyzate. The maltodextrin of the present invention is preferably employed as an aqueous solution having a solids content on the order of from about 70% by weight to about 75% by weight.

The aqueous solutions are generally prepared by adding the appropriate amount of cold water to the maltodextrin powder and mixing to form a paste.

The paste is then heated to a temperature of about 125° C. to form a solution and held at approximately that temperature until the solution clears.

The ingredients were stirred thoroughly over medium heat and allowed to cook to a temperature on the order of 125° C. Generally, the boiling point of any liquid is lower as the altitude increases, and the requisite cooking time is proportionally lengthened as the altitude increases.

The resultant mixture was found to be homogenous and easily pourable when allowed to cool 50° C. to 60° C. At that point, the mixture was removed from the vat and poured into appropriate containers. Upon further cooling to room temperature in the individual containers, the product was readily pliable and easy to work. In that condition, the product when stored in individual closed containers has been found to have excellent shelf life and can be stored for an indefinite period of time preliminary to use. In accordance with well-known practice, preservatives such as potassium sorbate and citric acid are added to the composition; the citric acid, i.e., lemon juice in addition minimizes any tendency of the sugar to crystallize when stored over long periods of time.

Typically, the product is best removed from the container by scooping out with the fingers. A few drops of water may be placed on the hands as a preliminary to removing the product so as to avoid any tendency of the product to stick to the hands and to make it more pliable or alternatively the product may be warmed to a temperature of about 50° C. The portion removed should be pulled and stretched or kneaded by hand until soft enough to readily apply to the skin with the fingers. For the purpose of applying, a small quantity is placed on the index and middle fingertips of one hand and then pressed into the skin along that section where the hair is to be removed. Extreme pressure is not required although it may be desirable to go over the same area two to three times to assure uniform adherence of the wax along the strip from which the hair is to be removed. In this relation, it is advisable to apply but a limited quantity to an area on the order of 0.5" to 1" wide and 2" to 3" in length. Immediately following application to the skin, the strip of material is then quickly pulled off by hand much in the manner of removing a bandaid from the skin. The application procedure is then repeated as described over or along adjacent strips where the hair is to be removed. Once removed, a wet cold towel or washcloth may be applied to the effected area to close the pores and to soothe the skin. Very little pain is experienced in the process of hair removal with no resultant swelling or irritation beyond that which would be normally experienced in plucking individual hairs from the skin. Any redness or discoloration caused by removal of the hair is found to disappear within twenty-four hours.

The composition may be mixed and prepared in any desired quantities. Of particular importance is the heating procedure to insure that the ingredients are heated to a temperature just below that at which the material will tend to harden. It has been found that the optimum temperature was 125° C. and the optimum cooking period, depending on batch size, on the order of 1.5 to 2 hours. When cooked to any appreciable extent below the hardening temperature, it was found that the consistency and homogeneity of the mixture were not as good. Even more critical, when boiled or cooked above or to the hardening point, the resultant mixture was virtually impossible to work even to the extent of removing it from the cooking vat.

In the Examples which follow, compositions of the present invention are exemplified:

EXAMPLE I

|  | % W/W |
| --- | --- |
| Maltodextrin (Maltrin QD. 500) | 5.0 |
| Sucrose | 70.0 |
| Water | 24.4 |
| Citric Acid | 0.5 |
| Potassium Sorbate (Sorbistat K) | 0.1 |
|  | 100.0% |

EXAMPLE II

|  | % W/W |
| --- | --- |
| Maltodextrin (Maltrin QD. 500) | 5.0 |
| Sucrose | 70.0 |
| Water | 19.9 |
| Citric Acid | 0.5 |
| Potassium Sorbate (Sorbistat K) | 0.1 |
| Glycerine U.S.P. | 4.5 |
|  | 100.0% |

The methods used in the preparation of the compositions is as follows: An aqueous paste is generally prepared by combining water with the maltodextrin and the resultant paste is then heated to a temperature of about 125° C. to form a solution which is then held at that temperature until the solution clears. The remaining components are added to the clear solution and heated with stirring to a temperature just below the hardening temperature of the composition, i.e. about 125° C. for from about 1.5 hours to about 2 hours.

With respect to all of the working Examples described, the wax product once cooked was allowed to cool to about 50° C., then poured into appropriate containers and the product was permitted to cool further until it hardened to the desired consistency. The resultant product was found to be easy to apply to the skin but with sufficient adherence to effectively remove the hair when lifted from the skin.

Generally, in applying to the skin for the purpose of hair removal, the skin should be dry and free of oils and creams.

The fingertips may be wetted and the desired amount of the product to be applied should be removed from the container with the fingertips. Holding the index and middle fingers together, the wax is spread in strips on the skin by pressing down firmly, going over the same section two to three times if desired. The strip of material is then pulled off quickly by lifting much in the manner or approach used to remove a bandaid.

After applying the wax over a desired area and removing as described, a cold wet towel or washcloth is applied to the treated area for a limited period of time to close the pores and to soothe the skin, after which a skin lotion may be applied if desired.

It has been found that in actual use in treating patients for hair removal the preferred substance can be quickly and easily applied in thin strips over closely controlled areas and is sufficiently viscous as not to tend to overrun or spread beyond the strip as applied. This is important, for example, in removal of facial hair, such as, along the eyebrow region so as to leave a well-defined line of demarcation between the eyebrow and adjacent area from which the hair has been removed. Nevertheless, the substance when handled as described is pliable and exhibits excellent adherence qualities when applied in strip form so as to assure complete removal of the hair from its roots without repeated applications. The formulation has demonstrated long-lasting effects in hair removal so that the process need not be repeated for weeks at a time.

It is therefore to be understood that various modifications and changes may be made in the specific composition, method of preparing and applying same without departing from the spirit and scope of the present invention as defined by the appended claims.

What is claimed is:

1. A depilatory composition for the removal of hair from the human skin wherein the composition is to be applied to a portion of human skin from which the hair is to be removed, said composition comprising from about 5% to about 30% by weight of maltodextrin, from about 45% to about 70% by weight of sucrose and from about 0.025% to about 1% by weight of citric acid said sucrose, maltodextrin and citric acid being intermixed and heated to a temperature just below the hardening point of the composition so as to have a waxy consistency as a preliminary to application to the human skin.

2. A depilatory composition according to claim 1, wherein said sucrose and maltodextrin are present in the approximate ratio of one part by weight of maltodextrin for each fourteen parts by weight of sucrose.

3. A depilatory composition according to claim 1, wherein said citric acid is added in the form of lemon juice.

4. The method of preparing a composition for the removal of hair from human skin and of applying the composition to a portion of human skin from which hair is to be removed comprising the steps of:

intermixing from about 5% to about 30% by weight of maltodextrin, from about 45% to about 70% by weight of sucrose and from about 0.0253 to about 1.0% by weight of citric acid;

heating said sucrose, maltodextrin and citric acid to a temperature level just below the hardening point of the mixture and holding the composition at approximately that temperature level without hardening the composition;

cooling the mixture to room temperature; and manually applying the mixture in thin strips to the skin followed by removing each strip so applied immediately after application to the skin.

5. The method according to claim 4, further characterized by heating the mixture during the heating step to a temperature on the order of 125° F.

6. The method according to claim 4, wherein said mixture is held at a temperature level just below the hardening point of the mixture for a period of from about one and one-half to about two hours.

* * * * *